United States Patent
Marka (10) Patent No.: US 7,465,065 B2
(45) Date of Patent: Dec. 16, 2008

(54) OPERATING TABLE LAMP

(75) Inventor: Rudolf Marka, Munich (DE)

(73) Assignee: Trumpf Medizin Systeme GmbH + Co. KG, Puchheim (DE)

( * ) Notice: Subject to any disclaimer, the term of this patent is extended or adjusted under 35 U.S.C. 154(b) by 55 days.

(21) Appl. No.: 11/067,590

(22) Filed: Feb. 28, 2005

(65) Prior Publication Data

US 2005/0195599 A1     Sep. 8, 2005

(30) Foreign Application Priority Data

Feb. 28, 2004    (EP)    .................... 04004601

(51) Int. Cl.
 F21V 1/08    (2006.01)
(52) U.S. Cl. .................. 362/232; 362/33; 362/572; 362/285; 362/418; 362/804
(58) Field of Classification Search ........... 362/252, 362/250, 235, 552, 572, 804, 232, 238, 239, 362/285, 372, 362, 371, 418, 449, 33
See application file for complete search history.

(56) References Cited

U.S. PATENT DOCUMENTS

| | | | | |
|---|---|---|---|---|
| 1,250,765 A | * | 12/1917 | Ballard et al. ............... | 362/250 |
| 1,960,534 A | * | 5/1934 | Gibney ........................ | 362/232 |
| 2,045,013 A | * | 6/1936 | Howland .................... | 362/253 |
| 4,196,460 A | | 4/1980 | Schreckendgust | |
| 5,951,139 A | | 9/1999 | Smith et al. | |
| 6,120,164 A | * | 9/2000 | Libin et al. ................. | 362/269 |
| 6,170,963 B1 | | 1/2001 | Arnold | |
| 6,435,693 B1 | | 8/2002 | Fiene | |
| 6,513,962 B1 | | 2/2003 | Mayshack et al. | |
| 6,585,395 B2 | * | 7/2003 | Luk ........................... | 362/250 |
| 2003/0146719 A1 | | 8/2003 | Laerum et al. .............. | 315/294 |
| 2003/0185009 A1 | | 10/2003 | Walters | |

FOREIGN PATENT DOCUMENTS

| | | |
|---|---|---|
| DE | 84 05 380 U1 | 5/1984 |
| DE | 197 29 758 | 1/1999 |
| DE | 100 34 594 | 1/2002 |
| DE | 201 16 750 U | 1/2002 |
| DE | 202 14 879 U | 10/2003 |
| FR | 947482 * | 7/1949 |

OTHER PUBLICATIONS

Brandon Medical Ltd. Galazy Ultra Brochure, Jul. 11, 1998, 10 pages.
Brandon Medical Ltd. Galaxy Ultra 53 Operating Theatre Light Specification Sheet, Apr. 20, 1998, 1 page.

* cited by examiner

*Primary Examiner*—Sandra O'Shea
*Assistant Examiner*—Bao Q. Truong
(74) *Attorney, Agent, or Firm*—Fish & Richardson P.C.

(57) ABSTRACT

An operating lamp for illumination of an illumination field includes a plurality of individual light modules connected together to form a light source. Each module includes a housing and at least one illumination means disposed in the housing. The housings include a surface having mechanical connectors adapted for coupling to the housing of an adjacent light module and electrical connectors adapted for controlling the illumination means and for connecting the illumination means to an electrical current supply.

17 Claims, 6 Drawing Sheets

OPERATING TABLE LAMP

CLAIM OF PRIORITY

This application claims priority under 35 USC §119(a) to European Patent application number 04004601, filed on Feb. 28, 2004, the entire contents of which are hereby incorporated by reference.

TECHNICAL FIELD

This disclosure relates to an operating table lamp.

BACKGROUND

Large mirror lamps (e.g., as disclosed in German Patent No. DE 197 29 758 A1) have the disadvantage that they include obstacles in the illumination field, which impair the shape of the illumination field, because a path between the light emitting surface of the lamp and the illumination field is interrupted by the obstacle. In resolved light systems (e.g., as disclosed in German Patent "Gebrauchsmuster" No. DE 84 05 380 U1), individual smaller light emitting surfaces suffer from an loss in illuminance through shadows cast by the operating surgeon. Furthermore, prior art operating lamps do not provide for a change of shape of the illumination field depending on the application (the area illuminated on the operating table).

SUMMARY

The invention is based, at least in part, on the recognition that an operating lamp with a uniform illumination field that can be adapted to various operations can be produced from combinable modules. An operating surgeon can adjust the modules to change the illumination field from the lamp according to his or her light requirements.

In a general aspect, an operating lamp for illumination of an illumination field includes a plurality of individual light modules connected together to form a light source. Each module includes a housing and at least one illumination means disposed in the housing. The housings include a surface having mechanical connectors adapted for coupling to the housing of an adjacent light module and electrical connectors adapted for controlling the illumination means and for connecting the illumination means to an electrical current supply.

Implementations can include one or more of the following features. For example, the at least one illumination means can be an LED. At least one pair of adjacent light modules can be pivotably connected to each other. Each module can further include at least one lens located between the illumination means and the illumination field, and the lenses can be adapted to provide uniform emission of light from the lamp and focus the light onto the illumination field.

The housing surface can be a side surface of the housing. The mechanical connectors can be adapted for connecting adjacent modules such that light output from the plurality of modules appears uniformly emitted from across the plurality of modules. The plurality of modules can form a concave surface facing the illumination field. A surface of each module facing the illumination field can form a concave surface facing the illumination field. A surface of each module facing the illumination field can be a flat surface facing the illumination field. The modules can be formed in the shape of hexagons that are connected together in a honeycomb structure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
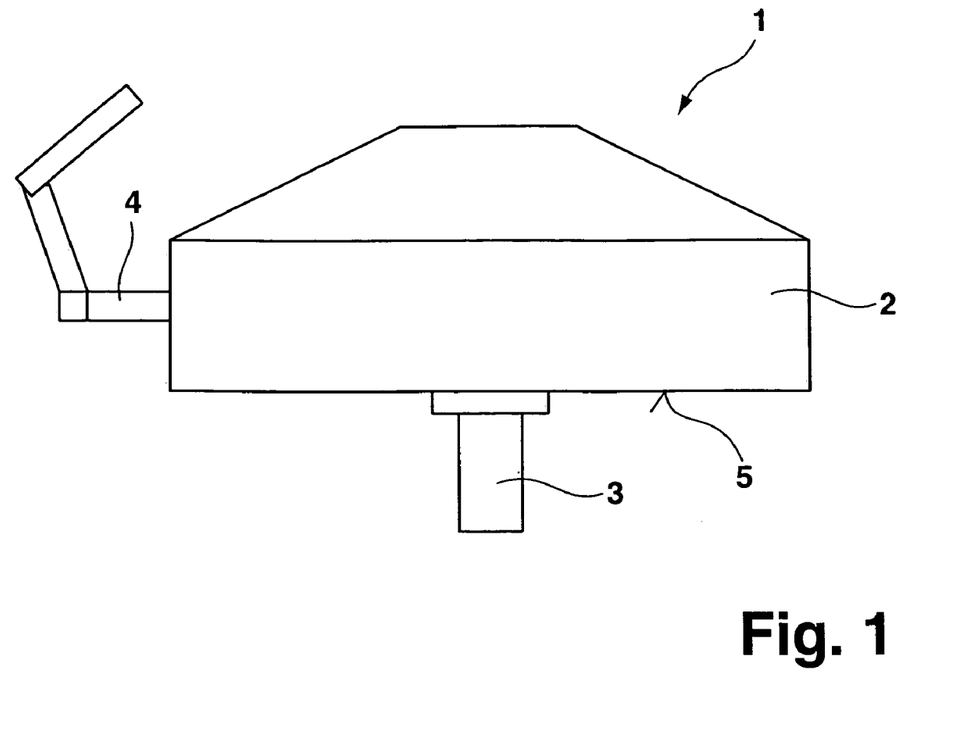
FIG. 1 is a schematic side view of an operating lamp.

As shown in FIG. 1, an operating lamp 1 includes a lamp body 2 having an inner space that houses an illumination means (not shown in FIG. 1). The lamp body 2 can be mounted on a stationary holder on a ceiling or wall of a building or on a mobile unit, such that it can be pivoted via a pivot arm (which is not completely shown in FIG. 1). The pivot arm is formed from several elements that are interconnected by joints. An element 4 of the pivot arm that is rigidly connected to the operating lamp 1 is indicated in FIG. 1. The operating lamp 1 can therefore be moved and pivoted in three dimensions in the X, Y, and Z directions. A handle 3 mounted to the lamp body 2 permits positioning of the operating lamp 1 at any location above an operating table. The handle 3 is detachably disposed on the lower side 5 of the operating lamp. Light is emitted on the lower side 5 of the operating lamp 1 to illuminate the area of an operation.

Figure 2:
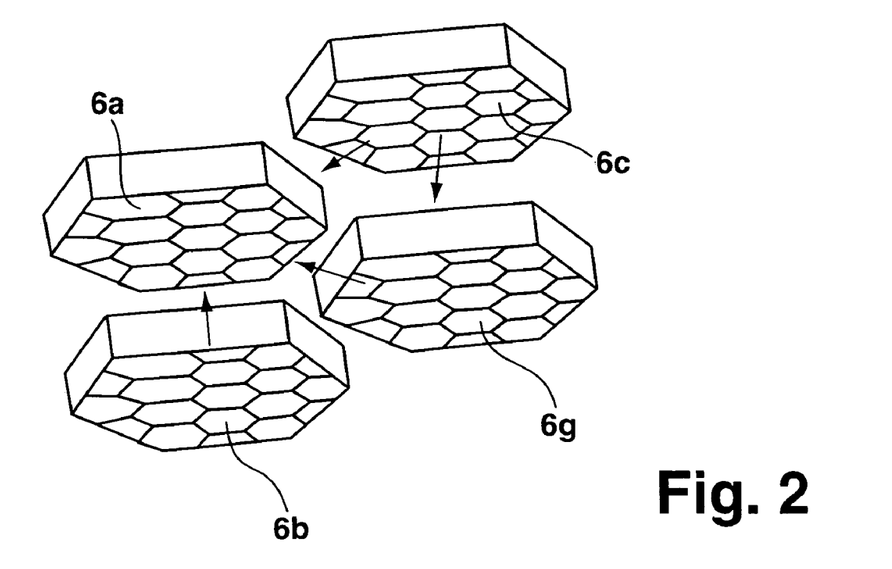
FIG. 2 is a schematic perspective view of several light modules of the operating lamp shown in FIG. 1.
Figure 3A:
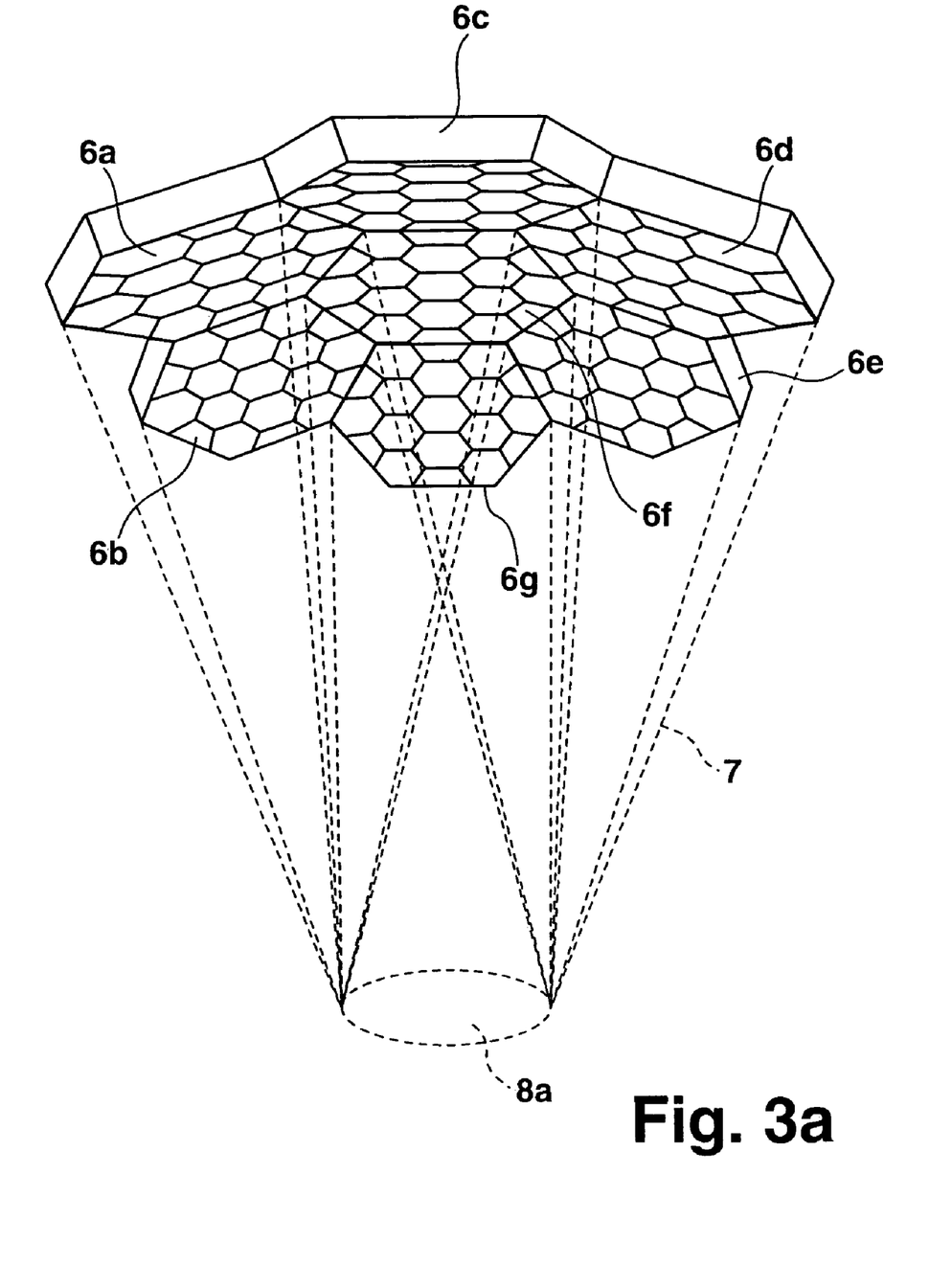
FIGS. 3a, 3b, 3c, and 3d are schematic perspective views of various combinations of the light modules of FIG. 2.
Figure 3B:
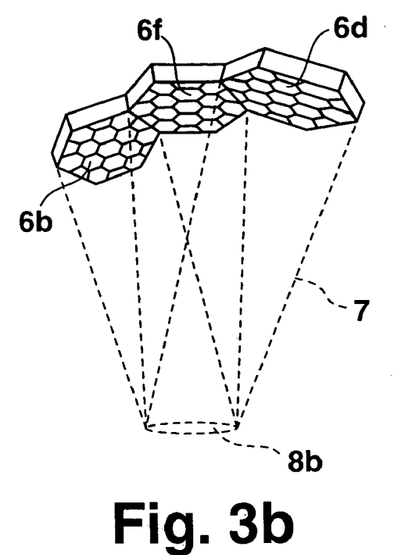
Figure 3C:
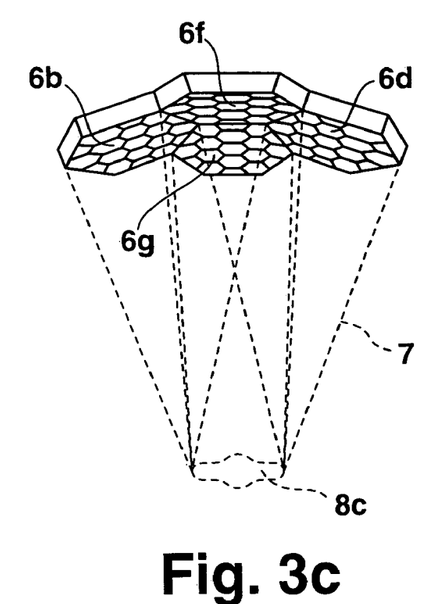
Figure 3D:
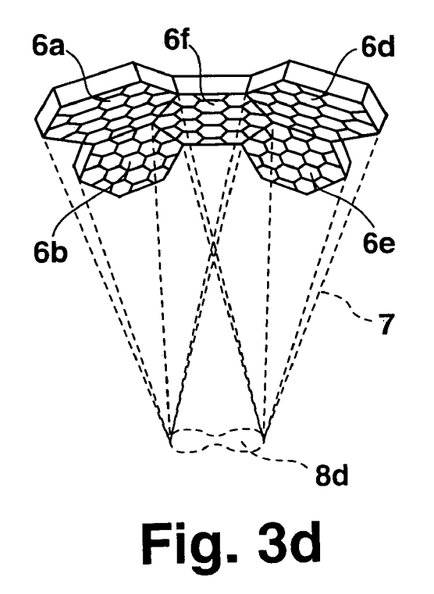

As shown in FIG. 2, individual light modules 6a, 6b, 6c, and 6g can be assembled as a light source, as indicated by the arrows in the figure. The individual light modules 6a, 6b, 6c, and 6g each includes a housing whose side surfaces 30 have mechanical, electronic, and electric connecting elements or connectors to control one or more illumination means in the light module and to connect the illumination means to an electric current supply. The light modules 6a, 6b, 6c, and 6g can be coupled to each other through any side surface, such that any possible combination of modules is feasible. Alternatively, modules 6a, 6b, 6c, and 6g can be mounted to a support plate 32, through mechanical, electronic, and/or electrical connecting elements or connectors on a rear side of the module to control one or more illumination means in the light module and to connect the illumination means to an electric current supply 34. Thus, with the combinable modules 6*a*, 6*b*, 6*c*, and 6*g*, it is possible to create a lamp 1 whose illumination field can be adjusted for the operation to be carried out.

As shown in FIGS. 3*a*, 3*b*, 3*c*, and 3*d*, modules 6*a*, 6*b*, 6*c*, and 6*g* can be combined and adjusted relative to each other to create custom illumination fields 8*a*, 8*b*, 8*c*, and 8*d* through the combination of light beams 7 emitted from the modules. Depending on the combination of the light modules 6*a*, 6*b*, 6*c*, and 6*g*, the illumination field 8*a*, 8*b*, 8*c*, and 8*d* can have a larger longitudinal or transverse extension. The illumination fields 8*a*, 8*b*, 8*c*, and 8*d* can have different structures at their edges or in their centers, and the various illumination fields 8*a*, 8*b*, 8*c*, and 8*d* can correspond to the various contours of the light module combinations. Each light module 6*a*, 6*b*, 6*c*, and 6*g* can illuminate one full operating location by itself. The illumination fields 8*a*, 8*b*, 8*c*, and 8*d* can be on a surface on the operating table that is illuminated. The light modules 6*a*, 6*b*, 6*c*, and 6*g* can be combined to form a light source through any combination of modules or with additional light modules to create various illumination fields of various sizes, shapes, and brightness.

Figure 4A:
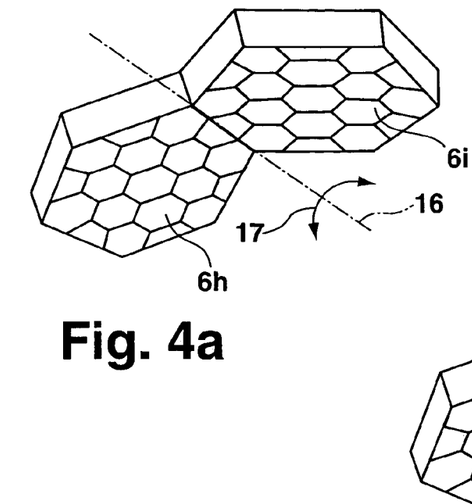
FIGS. 4a and 4b are schematic perspective views of a pivotable combination of light modules.
Figure 4B:
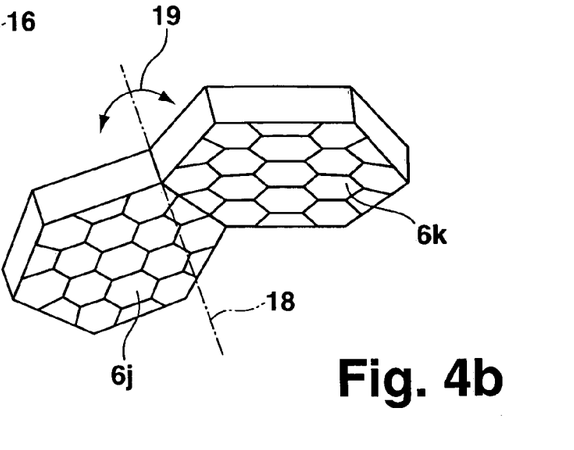

As shown in FIGS. 4*a* and 4*b*, the light modules 6*h*, 6*i*, 6*j*, and 6*k* are not rigidly connected to each other, but are pivotably coupled to each other using pivoting connections. These connections between adjacent modules 6*h* and 6*i*, and 6*j* and 6*k*, permit movement of the adjacent modules about a pivot axis 16 and 18 in the direction shown by double arrows 17 and 19. FIG. 4*a* shows that the side surfaces where the light exits, can be folded onto each other. As shown in FIG. 4*b* the edge surfaces 30 of adjacent modules 6*h* and 6*i* can be folded toward each other. In addition to the illustrated hinge-like joints at any connecting line of the light modules (as shown in FIG. 4*a*), ball and socket joints at one or more of the six corners of the light modules 6*h*, 6*i*, 6*j*, and 6*k* are feasible, allow adjacent modules 6*j* and 6*k* to pivot about an axis, as shown in FIG. 4*b*. The joints between adjacent modules 6*h*, 6*i*, 6*j*, and 6*k* allow the position of a light module to be changed relative to each other light module. Additional variation of the illumination fields by the operating surgeon is also possible. The pivoting axes between modules 6*h*, 6*i*, 6*j*, and 6*k* permits individual adjustments of the arrangement of the modules to change the illumination field 8*a*, 8*b*, 8*c*, and 8*d*.

The light modules 6*a-k* can be joined practically seamlessly, such that joints between the individual light modules 6*a-k* have no substantial influence on the optical properties of the light generated by the combination of the modules, in particular, on the light output in the direction of the operating location. Thus, the generated light from the combination of light modules 6*a-k* is perceived as being uniform although the light source includes several light modules 6*a-k*.

Figure 5:
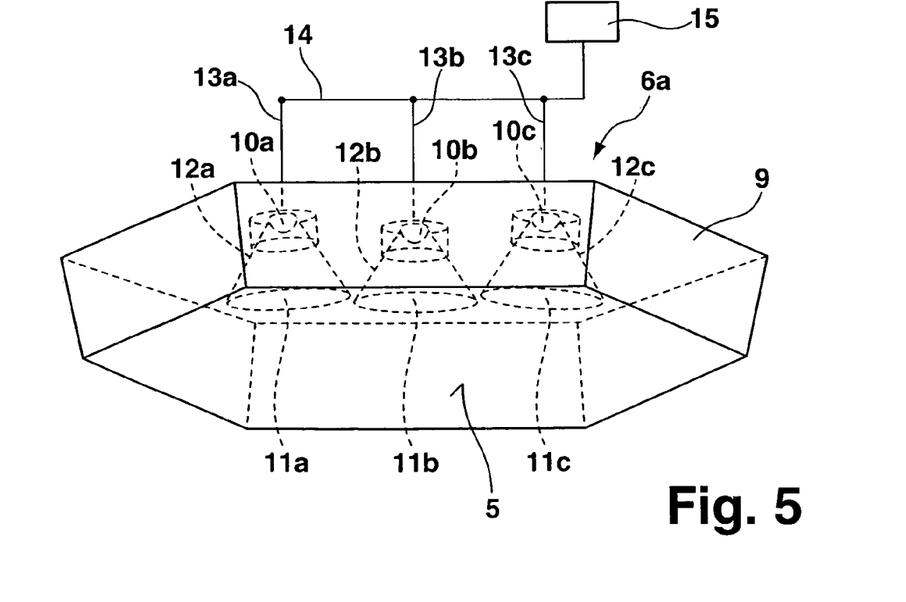
FIG. 5 is a detailed schematic perspective view of the light module of FIG. 2.

As shown in FIG. 5, an individual light module 6*a* can include a plurality of individual light emitting diodes ("LEDs"). For example the light source and include 5, 10, 25, or 50 or more LEDs. A large number of LEDs can be advantageous compared to large mirror lamps, in that a light source composed of LEDs creates a large-surface light source that minimizes shadows.

The light module 6*a* can include a housing 9 having mechanical and/or electrical or electronic connecting elements or connectors for connecting the module to a neighboring light modules 6*b-g*. The shape of the light modules 6*a-g* is designed such that the plurality of modules can be disposed on a curved (e.g., spherical) surface of a typical radius of about 1000 mm without substantial gaps between adjacent modules. Towards this end, the light modules 6*a-g* can be designed as hexagons, such that when assembled a type of honeycomb structure or facetted structure is obtained. The surface of the light modules 6*a-g* facing the operating location need not necessarily be flat, but may be slightly concave to improve reproduction of a spherical surface, and the optical axis of each light module 6*a-g* can face towards the focus of the spherical surface.

Different shapes of the illumination field 8 can be generated by combining light from modules 6*a-g* oriented at different setting angles. Towards this end, also intermediate elements may be used. Multiple (e.g., 5, 10, 20, 30, or even 50 or more) LEDs can be evenly distributed in each light module 6*a-g*, and three LEDs 10*a-c* are shown in FIG. 5. Although light sources 10*a-c* are shown as LEDs in FIG. 5, other light sources can be used instead of LEDs (e.g., halogen lamps, gas discharge lamps, incandescent lamps, and liquid crystals). Formation of shadows is optimized through planar emission of light from the LEDs 10*a-c*. Towards this end, each of the nearly point source LEDs 10*a-c* can be associated with suitable optical elements (e.g., lenses 11*a-c*), such that light beams 12*a-c* are emitted from the LEDs 10*a-c*, respectively. The shape of the optical elements 11*a-c* is designed such that they fill the light module 6*a* preferably to the edges of the module 6*a*. The lens elements 11*a-c* can also have a scattered structure to make the illumination field more homogeneous. The lower side 5 of the light module 6*a* can be covered by a transparent plate.

The combination of individual light modules 6*a-g* can form a light source having a various color temperatures, for example, approximately 4500 K, and a color reproduction index Ra of greater than or equal to about 93 to obtain natural color representation of an illuminated object (e.g., of the tissue to be operated on). For this reason, not only white-light LEDs are used but also LEDs that generate colored light. The addition of colored light, such as cyan and blue, minimizes a decline in the relative amount of short-wavelength light in the spectrum of light reflected from the illuminated object, as can be the case with purely white light. With a constant brightness of the white LEDs in the light source, the color temperature and color reproduction of the mixed light, which is generated by the overall light source, consisting of all individual light modules 6*a-g* can be variably adjusted. The light flux intensity of the colored LEDs can be continuously changed by selectively dimming of the intensity of the colored LEDs. The LEDs 10*a-c* can be connected to a controller 15 (e.g., a current controller) through current lines 13*a-c* and 14. The electric dimming of the colored LEDs changes the color temperature and/or color reproduction and allows the operating surgeon to mix colored light and white light according to his or her requirements to emphasize special types of tissue or tissue changes through the light. Dimming may be provided through a change of the electric current and/or of the electric voltage supplied to the LEDs 10*a-c*. Alternatively, dimming of light from individual modules may be realized through mechanical and/or optical means, such as shutters, lenses or optical filters, which can be moved into the optical path to change the light flux. Through controllable dimming of light from the modules the operating surgeon is able to better recognize individual tissue types or tissue changes.

A basic setting of a color temperature of 4500 K can be predetermined for the light lamp 1 and automatically generated when the operating lamp is switched on. Other desired color temperatures, depending on the application of the operating lamp 1, can be adjusted by the operating surgeon using a control panel or a keyboard of the controller 15. The required setting parameters may be stored in a storage of the controller 15. It is also feasible for the operating surgeon to store further settings chosen by himself or herself, wherein these personal settings may also be changed later.

Figure 6:
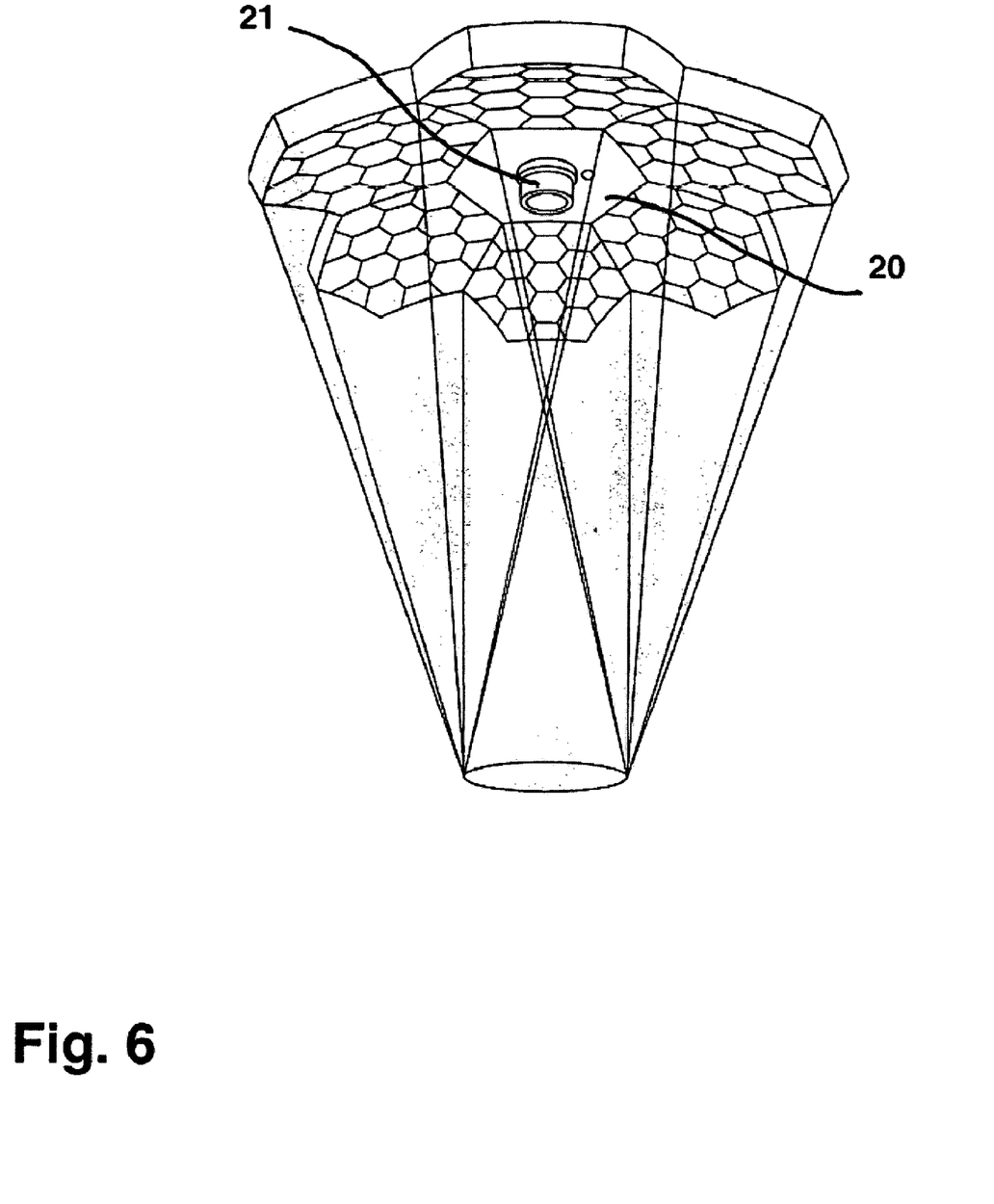
FIG. 6 is a schematic perspective view of a combination of light modules.

As shown in FIG. 6, additional modules can also be included in the lamp 1. For example, a camera module 20 can be combined with light modules 6a-k and can be used to support a camera for recording still or moving images of the illumination field. Through insertion of the module 20 into the combination of modules 6a-k, the required electric connections to the module 20 necessary for image processing are automatically generated.

Figure 7:
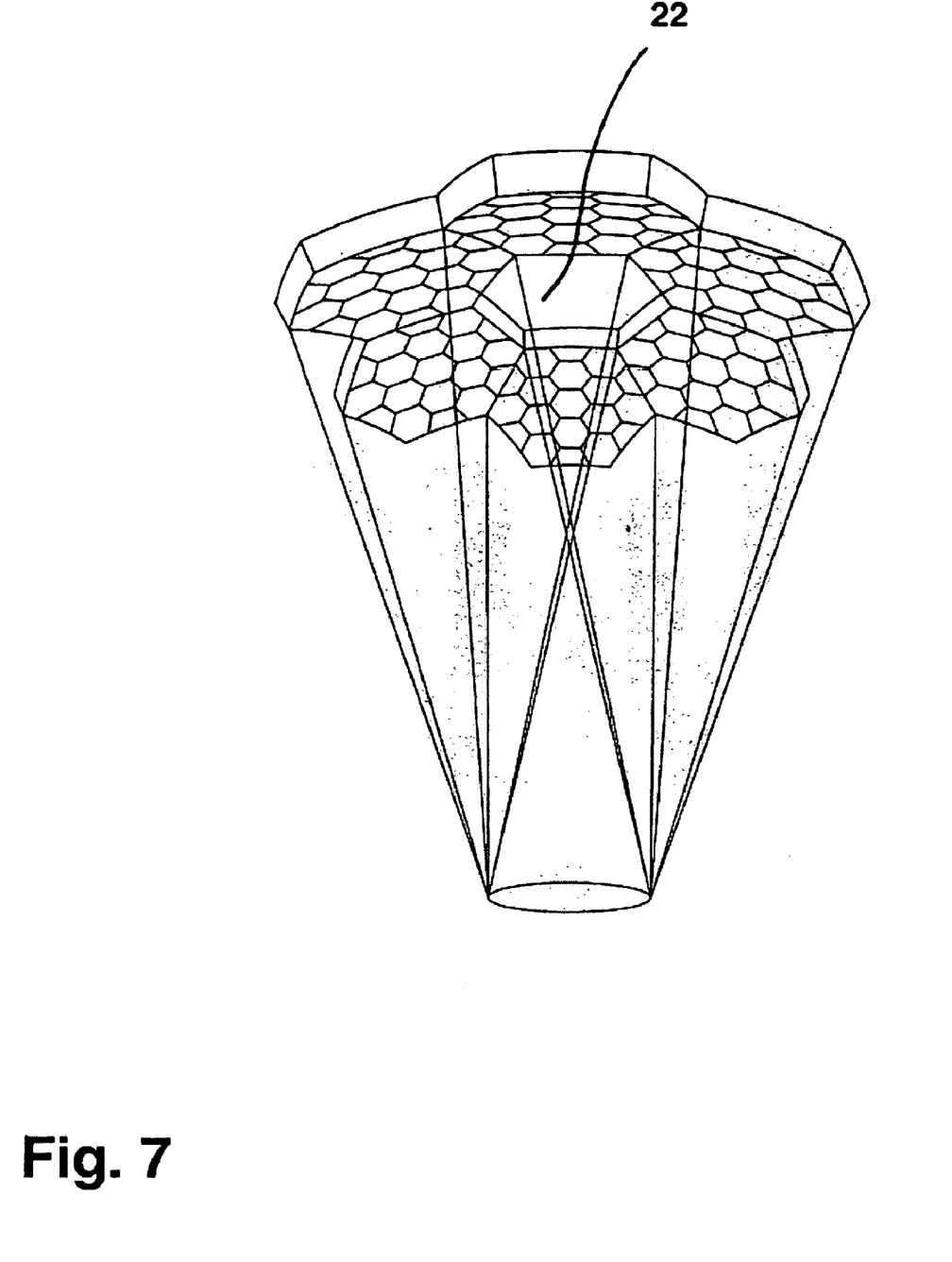
FIG. 7 is another schematic perspective view of a combination of the light modules.

As shown in FIG. 7, a space 22 may be provided in a combination of modules 6a-k (e.g., in the center of the operating lamp 1) to reduce the influence of the lamp 1 on existing ventilation in the ceiling in the operating room. The space 22 is produced through omission of a central module on the combination of modules.

OTHER EMBODIMENTS

A number of embodiments of the invention have been described. Nevertheless, it will be understood that various modifications may be made. Accordingly, other embodiments are within the scope of the following claims.

What is claimed is:

1. An operating lamp for illumination of an illumination field comprising:
   a plurality of individual light modules connected together to form a light source, each module comprising a housing and at least one light emitting element disposed in the housing, the housing of each light module being connected directly to the housing of an adjacent light module,
   wherein the housing of each light module comprises a surface having (a) one or more mechanical connectors configured to couple the housing directly to the housing of an adjacent light module and (b) one or more electrical connectors configured to control the light emitting element(s) and connect the light emitting element(s) to an electrical current supply, the connectors being configured so that the position of each module relative to each other module can be adjusted by a user, allowing the user to adjust the illumination field according to the user's requirements.

2. The operating lamp of claim 1, wherein the at least one light emitting element is an LED.

3. The operating lamp of claim 1, wherein at least one pair of adjacent light modules are pivotably connected to each other.

4. The operating lamp of claim 1, wherein each module further comprises at least one lens located between the light emitting element(s) and the illumination field, and wherein the at least one lens in each module is adapted to provide uniform emission of light from the lamp and focus the light onto the illumination field.

5. The operating lamp of claim 1, wherein the surface is a side surface of the housing.

6. The operating lamp of claim 1, wherein the mechanical connectors are adapted for connecting adjacent modules such that light output from the plurality of modules appears uniformly emitted from across the plurality of modules.

7. The operating lamp of claim 1, wherein the plurality of modules forms a concave surface facing the illumination field.

8. The operating lamp of claim 1, wherein a surface of each module facing the illumination field forms a concave surface facing the illumination field.

9. The operating lamp of claim 1, wherein a surface of each module facing the illumination field is a flat surface facing the illumination field.

10. The operating lamp of claim 1, wherein the modules are formed in the shape of hexagons that are connected together in a honeycomb structure.

11. The operating lamp of claim 1, wherein the modules are shaped so that the modules can be disposed on a generally spherical surface without substantial gaps between the modules.

12. The operating lamp of claim 1, further comprising a controller configured to adjust the light modules to adjust the color temperature of the light source.

13. The operating lamp of claim 12, wherein the controller is configured to allow a user of the operating lamp to vary the color temperature.

14. The operating lamp of claim 5, wherein at least one pair of adjacent light modules are pivotably connected to each other, and the pivotable connection is configured to allow the side surfaces of the modules to be folded toward each other.

15. The operating lamp of claim 1, wherein the light emitting element comprises a light source selected from the group consisting of halogen lamps, gas discharge lamps, incandescent lamps, and liquid crystals.

16. The operating lamp of claim 1, further comprising a controller configured to allow the modules to be selectively dimmed.

17. The operating lamp of claim 1, wherein at least some of the modules are directly connected to at least two adjacent modules.

* * * * *

UNITED STATES PATENT AND TRADEMARK OFFICE
CERTIFICATE OF CORRECTION

| | | |
|---|---|---|
| PATENT NO. | : 7,465,065 B2 | Page 1 of 1 |
| APPLICATION NO. | : 11/067590 | |
| DATED | : December 16, 2008 | |
| INVENTOR(S) | : Rudolf Marka | |

It is certified that error appears in the above-identified patent and that said Letters Patent is hereby corrected as shown below:

Col. 6, line 18, Claim 9, please delete "fiat" and insert --flat--.

Signed and Sealed this

Twelfth Day of January, 2010

David J. Kappos
*Director of the United States Patent and Trademark Office*